(12) United States Patent
Li et al.

(10) Patent No.: US 10,239,806 B2
(45) Date of Patent: Mar. 26, 2019

(54) CONTINUOUS SOLID-STATE SEPARATION DEVICE AND PROCESS FOR PRODUCING FUEL ETHANOL

(71) Applicant: TSINGHUA UNIVERSITY, Beijing (CN)

(72) Inventors: Shizhong Li, Beijing (CN); Guangming Li, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 530 days.

(21) Appl. No.: 14/958,563

(22) Filed: Dec. 3, 2015

(65) Prior Publication Data

US 2016/0083320 A1    Mar. 24, 2016

Related U.S. Application Data

(63) Continuation of application No. PCT/CN2014/071587, filed on Jan. 27, 2014.

(30) Foreign Application Priority Data

Aug. 7, 2013  (CN) .......................... 2013 1 0341927

(51) Int. Cl.
*B01D 3/08* (2006.01)
*C07C 29/84* (2006.01)
(Continued)

(52) U.S. Cl.
CPC .............. *C07C 29/84* (2013.01); *B01D 3/002* (2013.01); *B01D 3/004* (2013.01); *B01D 3/38* (2013.01);
(Continued)

(58) Field of Classification Search
CPC .......... B01D 3/002; B01D 3/004; B01D 3/08; B01D 3/38; C07C 29/80; C07C 29/84
See application file for complete search history.

(56) References Cited

U.S. PATENT DOCUMENTS 7,032,893 B2 *  4/2006  Sotoyama ................ A23C 7/04
                                                                261/89
8,266,812 B2 *  9/2012  Weisselberg ............ C10L 9/083
                                                                110/218
(Continued)

FOREIGN PATENT DOCUMENTS

CN          101633940 A      1/2010
CN          101724661 A      6/2010
(Continued)

OTHER PUBLICATIONS

CN 101235391B, Shzhong et al., Method and system for continuously separating ethanol and utilizing residual heat based on solid-state fermentation material, 2011, English abstract 2 pages.*
(Continued)

*Primary Examiner* — Jonathan Miller
(74) *Attorney, Agent, or Firm* — Locke Lord LLP; Tim Tingkang Xia, Esq.

(57) ABSTRACT

The present invention belongs to the technology field of microbial fermentation of the sugar-containing raw materials for producing fuel ethanol. It specifically relates to a continuous separation device and process for producing fuel ethanol. The device is continuous distillation device, and is improvement of the distillation device in the prior art. The present invention utilizes a continuous ethanol separation process, which can make full use of fermentable sugar of the sweet sorghum straw (or sugar cane, sugar beet), increase ethanol yield, change the traditional mode of production, truly realize continuous ethanol separation process; and the waste materials produced in the procedure of distillation can be used either as fuel, or as animal feed, and this not only saves the cost, but also is greatly significant in environmental protection.

6 Claims, 1 Drawing Sheet

(51) Int. Cl.
    *C12M 1/00*   (2006.01)
    *B01D 3/00*   (2006.01)
    *B01L 3/08*   (2006.01)
    *B01D 3/38*   (2006.01)
    *C07C 29/80*  (2006.01)

(52) U.S. Cl.
    CPC ............... B01L 3/08 (2013.01); C07C 29/80 (2013.01); C12M 21/12 (2013.01); C12M 43/02 (2013.01); C12M 47/10 (2013.01); C12M 47/20 (2013.01); Y02E 50/17 (2013.01)

(56) References Cited

U.S. PATENT DOCUMENTS

| | | | | |
|---|---|---|---|---|
| 8,276,289 B2 * | 10/2012 | Causer | ............... | C10B 49/02 |
| | | | | 122/22 |
| 8,500,105 B2 * | 8/2013 | Nieuwoudt | ............ | B01D 3/205 |
| | | | | 261/79.2 |
| 8,549,769 B2 * | 10/2013 | Weisselberg | ............ | C10L 9/083 |
| | | | | 110/218 |
| 9,062,255 B2 * | 6/2015 | DePouli | ................... | C10B 7/02 |

FOREIGN PATENT DOCUMENTS

| | | | |
|---|---|---|---|
| CN | 102094045 A | | 6/2011 |
| CN | 101235391 B | * | 8/2011 |
| CN | 103509713 A | | 1/2014 |
| JP | 2011030504 A | | 2/2011 |

OTHER PUBLICATIONS

State Intellectual Property Office of the P.R. China (ISR/CN), "International Search Report for PCT/CN2014/071587", China, dated May 26, 2014.

* cited by examiner

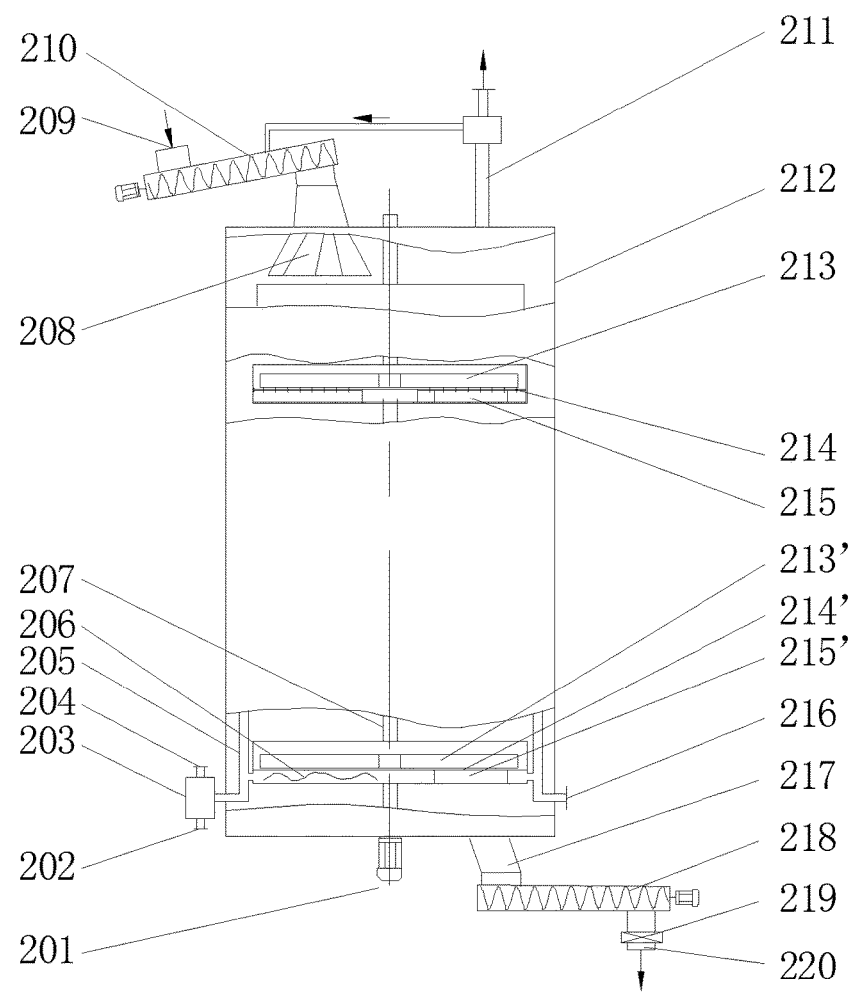

CONTINUOUS SOLID-STATE SEPARATION DEVICE AND PROCESS FOR PRODUCING FUEL ETHANOL

CROSS-REFERENCE TO RELATED APPLICATIONS

This application is a continuation application of International Patent Application No. PCT/CN2014/071587, filed Jan. 27, 2014, which itself claims priority to Chinese Patent Application No. 201310341927.7, filed Aug. 7, 2013, which are incorporated herein by reference in their entireties.

TECHNICAL FIELD

The present invention belongs to the technology field of microbial fermentation for producing fuel ethanol. It specifically relates to a continuous separation device and process for producing fuel ethanol, particularly to a continuous separation device and process for producing fuel ethanol from sugar-containing raw materials.

BACKGROUND OF THE INVENTION

With the development of the society, the fossil resources have gradually depleted, countries around the world begin working on renewable energy materials, and a new green energy—fuel ethanol, which can be used to replace fossil fuel, has been widespread concern at home and abroad. Because its combustion characteristics are very close to gasoline, fuel ethanol can be used by being blended with gasoline in certain proportion, and can also be used directly as a fuel, greatly reducing harmful gas emissions. Fuel ethanol has a broad development space.

As the world population increase rapidly, in order to ensure food supply, some countries gradually begin to apply policies restricting the production ethanol from food crops, thus producing ethanol from non-food crops will become a trend. Sweet sorghum, for its characteristics such as drought resistance, salt and alkali resistance, high adaptability, and high sugar content of the stem, becomes a preferred candidate of such non-food crops.

There are mainly two ways of liquid- and solid-state fermentations for producing ethanol from sweet sorghum straws. The liquid fermentation is to ferment the juice squeezed from fresh sweet sorghum straws; however, the preservatives added necessarily for juice storage will adverse to the fermentation yeast, and the squeezed solid material will contain a certain amount of residual sugar, both of which will decrease ethanol yield. The solid-state fermentation is to directly ferment crushed sweet sorghum straws, which simplifies the raw material pretreatment, avoids the use of preservatives, and reduces sugar loss, thus fundamentally overcoming the lacks of liquid fermentation.

However, most current solid state fermentation technologies still follow the traditional winemaking process, which is carried out in a fixed fermentation pool or tank, and is operated intermittently, and thus the alcohol is volatile, and the production efficiency is low. Also, the crushed straw material has the characteristics of intertwining, and thus it is difficult to realize the continuous flow, and the uncertainty of its movement also brings monitoring difficulties. Therefore, the top priority in developing the industry of producing fuel ethanol by biomass fermentation is to develop new device, reduce cost and energy consumption, increase ethanol yield, and achieve continuous solid-state fermentation.

It is also a technical difficulty existing in the art to simultaneously achieve continuous ethanol separation during the procedure of continuous solid-state fermentation. Because of the high mutual friction force of crushed straw fermentation materials of such as sweet sorghum, sugar cane, they are easy to tear and cake when moving, so it is difficult to realize continuous flowing, which together the characteristics of variability of its movement and the uneasy of detecting motion parameters make it a world difficulty to realize the continuous alcohol steaming using solid state fermentation materials. Therefore, the top priority in realizing the operation of continuous alcohol steaming during straw solid-state fermentation is to achieve the continuity of the alcohol steaming process using solid-state fermentation materials, to increase the concentration and stability of alcohol in gas phase, to improve production efficiency, and to reduce production cost and energy consumption.

In the Chinese patent application publication CN 102094045A, the inventors of the present invention disclosed a device and process for continuously separating ethanol from solid-state fermentation materials, the process comprising the following steps:

(a) The solid-state fermentation materials are fed into the inlet of the continuous alcohol steaming device by a screw conveyor for feeding; the materials uniformly distribute in the rotary grid on the surface of the uppermost heating disk by a distributor; in the heating disk is input with saturated steam of 0.1-1 MPa; and after be heated by the heating disk indirectly, the fermentation materials fall from its material outlet into the corresponding rotary grid on the heating disk of the next layer, continuously and orderly flow towards the outlet of the device, and discharge from a discharging outlet finally;

(b) After heating, the ethanol and water in fermentation materials partially vaporize into distillation gas, which discharges from a top vent, and directly enters into a rectifying tower for rectifying.

Alternatively, the saturated steam in the step (a) is replaced by thermally conductive high temperature oil steam or another hot gas.

Alternatively, the temperature in the continuous alcohol steaming device is kept at 100° C. or above.

The device for continuously separating ethanol from solid-state fermentation materials disclosed in the Chinese patent application publication CN 102094045A comprises a housing, a screw material feeder connecting with the inlet of the housing, a discharging bin connecting with the outlet of the housing and a screw material discharger, a spindle locating on the center axis of the housing and a driving motor connecting with the rotation shaft. Under the screw material feeder, the inner wall of the housing is provided with distributing plate grids, and plurality of heating disks connect in series with the rotation shaft; the heating disk is a hollow body made up by two plates and a side wall, the hollow body in the chamber is provided with steam folding baffles, and is input with water vapor; the heating disks on the sidewall is symmetrically provided with a steam inlet and a steam outlet, and the heating disk is provided with several fan-shaped holes for fermentation materials flowing; each of the heating disks is provided with a rotary grid; each of the steam outlets of the heating disks are connected with the main line of outflow steam via a square pipe, and the main line of outflow steam at the end is provided with a gas-liquid separator, to separate steam and condensate; the housing on the top is provided with a steam outlet, a condenser and a backflow tube which connects the condenser and the screw material feeder.

The heating disk is air-tightly sealed, and the steam can only flow in or out from the inlet and outlet on the heating disk; the feeding inlet and discharging outlet of the housing are both equipped with sealing apparatus, wherein the feeding inlet is sealed by fermentation material accumulation, and the discharging outlet is sealed with a gate valve or a flap valve or a multilayer flap valve, thus the entire device being air-tightly sealed.

The fan-shaped holes on the heating disk in the vertical direction successively shift a distance of the size of the fan-shaped hole opposite to the rotation direction of the rotary grid.

The temperature is kept via using thermal insulating materials on the outside wall of the housing, inputting steam into a jacket or using an electric heating zone, and the temperature is kept at 100° C. or above.

The distributing plate grid is a distributor consisting of several pieces of grid plates, and the fermentation materials inputted by the screw material feeder, after being distributed by the distributor, will be uniformly distributed in the rotary grid on the surface of the heating disk.

The rotary grid is made up by two cylinder plate grids connected via several of straight plate grids, the center of the rotary grid are fixed on the rotation shaft which goes throughout the center of each of the heating discs, and rotary grid rotates along with the rotation shaft.

However, the above device and process for continuously separating ethanol still have some defects, such as: 1. During the distillation procedure, the heating disks are used to heat the materials, and thus the heat transfer efficiency is not ideal; 2. The feeding inlet and discharging outlet have poor air-tight effect, and this makes the outflow of the distillation products; 3. The material thickness in the distillation tower is uneven, and this affects the distillation efficiency; 4. The moisture content of the distillated materials (residues) is high, and they cannot be reused and can only be discharged as industrial waste, which has an evil impact on the environment, etc.

Therefore, there remains a need in the art to achieve a device and process for continuously separating ethanol, so as to solve the problems of low ethanol production rate the difficulty in achieving continuity, and the serious environmental pollution during the current process of producing ethanol from the sweet sorghum straw.

SUMMARY OF THE INVENTION

In order to solve the above technical problems, in view of the flowing characteristics of the materials, combined with the operating characteristics of fermentation process, the present invention provides a continuous ethanol separation device and process for producing fuel ethanol, so as to realize the continuous production of fuel ethanol from the sweet sorghum straws.

On the one aspect, the present invention provides a device for continuously separating fuel ethanol from solid-state fermentation materials, the device comprising: a housing (212), a screw conveyor for feeding (210) connecting with the inlet of the housing (212), a discharging bin (217) and a screw conveyor for discharging (218) connecting with the outlet of the housing (212), a rotation shaft (207) locating on the center axis of the housing (212) and a driving motor (201) connecting with the rotation shaft (207), characterized in that: under the screw conveyor for feeding (210), the inner wall of the housing (212) is provided with distributing plate grids (208); the housing (212) along the longitudinal direction has alcohol distillation components and drying components, wherein the drying components are located under the alcohol distillation components and connect with the alcohol distillation components, which are composed of plurality of tower trays (214) connected in series with the rotation shaft, wherein the tower tray (214) is a disc with a tower tray fan-shaped hole (215), and each of the tower trays is provided with a tower tray rotary grid (213); the steam inlet of the alcohol distillation components is located at their bottom, and the steam outlet is located at their top; the drying components are composed of plurality of heating disks (214') connected in series with the rotation shaft, wherein the heating disk (214') is a hollow body made up by two plates and a side wall, and the chamber of the hollow body is provided with steam folding baffles (206), and is input with vapor; the heating disk (214') on the sidewall is symmetrically provided with a steam inlet and a steam outlet; each of the heating disks (214') is also provided with a heating disk rotary grid (213') and a heating disk fan-shaped hole (215') respectively; the steam inlets of the alcohol distillation components and the heating disks (214') are respectively connected with the main line for steam inputting (216), and the steam outlet of the alcohol distillation components is connected with the steam outlet (211) at the top of the housing, so that the steam directly enters into a rectifying tower for rectifying; the steam outlet of the drying components are connected with the main line for steam outputting (205) under the housing, and the main line for steam outputting (205) at the end is provided with a gas-liquid separator (203), to separate steam and condensate.

In an embodiment of the present invention, the fan-shaped holes on the tower trays and the heating discs in the vertical direction successively shift a distance of the size of the fan-shape hole opposite to the rotation direction of the rotary grid.

In an embodiment of the present invention, the temperature is kept via using thermal insulating materials on the outside wall of the housing, inputting steam into a jacket or using an electric heating zone, and the temperature is kept at 100° C. or above.

In an embodiment of the present invention, the distributing plate grid is a distributor consisting of several pieces of grid plates, and the fermentation materials inputted by the screw material feeder, after being distributed by the distributor, will be uniformly distributed in the rotary grid on the surface of the heating disc.

In an embodiment of the present invention, the rotary grid is made up by two cylinder plate grids connected by several of straight plate grids, the center of the rotary grid are fixed on the rotation shaft, which goes throughout the center of each of the heating discs, and the rotary grid rotates along with the rotation shaft.

On the other aspect, the present invention provides a continuous ethanol separation process for producing fuel ethanol, comprising the following steps:

(a) The solid-state fermentation straw materials are fed into a distributing plate grid 208 at the top of the device via a screw conveyor for feeding 210, the materials evenly distribute in the tower tray rotary grid 213 of the first layer of tower tray 214 at the top of the device and move along with it, to tower tray fan-shaped hole 215 of the tower tray and then fall onto the rotary grid of the second layer of tower tray, and so on until to the lowest layer of tower tray, during which the materials fully contact with steam to fulfill distillation. Through the lowest layer of tower tray, the materials fall onto the heating disc rotary grid 213' of the heating disc 214' and move along with it. When the materials move to the heating disk fan-shaped hole 215' of the heating disc 214', they fall onto the rotary grid of the next layer of heating disc, and so on until to the lowest layer of heating disc. On each of the heating discs 214', the materials do not contact with vapor, and are only heated by the heating discs to remove moisture, and through the plurality of heating discs 214', they are transferred to the discharging bin 217 at the bottom of the device. Then, the materials are outputted by the screw conveyor for discharging 218 and the double-layer flap valve 219, and the discharged materials are dried and recycled into a furnace to burn.

(b) In the meantime, saturated steam enters into the inside of the device via the main line for steam inputting 216 and spreads between each layer of tower trays and into the heating discs, the condensed water and the uncondensed steam after condensing and heat-releasing in the heating discs are collected by the main line for steam outputting 205, before entering into the gas-liquid separator 203, the uncondensed steam is reused for its exhaust heat, and the condensed water after collected enters into boiler through the water pipeline to the boiler. Along with the steam transferring heat to the materials, ethanol and water are heated and vaporized into vapor, and the vapor enters into a rectifying tower directly via the output of the steam outlet 211 for rectifying.

In an embodiment of the present invention, partial fermented waste materials generated in step (c) are used as animal feed.

The ethanol continuous separation device and process of the present invention have the following beneficial effects:

(1) The unique design of the alcohol distillation components and the drying components and their proper cooperation in technique with the rotary grids can realize continuously smooth flow of solid materials, making the procedure of alcohol distillation of the solid-state fermentation materials to be really continuous, thereby improving production efficiency, reducing labor intensity, and achieving the purpose of saving energy and reducing production cost.

(2) Through the direct contacting of steam and the materials, heat transfer efficiency is greatly improved, which makes the duration of alcohol distillation of continuous alcohol distillation process is shorten to less than half an hour at large production capacity, greatly improving production efficiency.

(3) The device and process of continuously separating fuel ethanol from solid-state fermentation materials can adjust its production capacity at a certain range by the rotational speed of grids, realizing the controlled and adjustable operation of production.

(4) The continuous operation makes a stable ethanol concentration in gas phase, providing convenience for further rectification and guaranteeing product quality.

(5) The distillated gas may directly enter into a rectification tower for rectification, omitting the step of condensing before entering into the rectification tower, thus saving energy and improving efficiency of rectification.

(6) Under the alcohol distillation components are installed with the drying components, which further reduce the water content of distillated waste materials (residues) produced in the step (c), and they are suitable to be as fuel sent into the distillation furnace and as animal feed, thus realizing the recycling of the waste materials. This not only saves production cost, reduces energy consumption, but also reduces the procedure of waste material treatment, thus being significant in environmental protection.

BRIEF DESCRIPTION OF DRAWINGS

FIG. 1 is a structural schematic of the continuous ethanol separation device of the present invention. The appended drawing reference signs in the FIGURE: 201—driving motor; 202—condensate outlet; 203—gas-liquid separator; 204—steam outlet; 205—main line for steam outputting; 206—steam folding baffle; 207—rotation shaft; 208—distributing plate grid; 209—inlet of the fermentation materials; 210—screw conveyor for feeding; 211—top steam outlet; 212—housing; 213—tower tray rotary grid; 213'—heating disc rotary grid; 214—tower tray; 214'—heating disk; 215—tower tray fan-shaped hole; 215'—heating disc fan-shaped hole; 216—main line for steam inputting; 217—discharging bin; 218—screw conveyor for discharging; 219—double-layer flap valve; 220—discharging outlet.

DETAILED DESCRIPTION OF THE INVENTION

The present invention provides a continuous solid-state fermentation and continuous separation device and process for producing fuel ethanol, to solve the problems of high pre-treating cost of liquid fermentation raw materials, low ethanol production rate and low production efficiency of solid-state fermentation, and the difficulty in achieving continuity during the current process of producing ethanol from the sweet sorghum straws, realizing continuous production of fuel ethanol from sweet sorghum straws.

In an embodiment of the present invention, except partial fermented waste materials (residues) produced in step (c) are sent into a distillation furnace to burn, the others are used as animal feed. This realizes the full use of waste materials. This not only saves production cost, reduces energy consumption, but also is greatly significant in environmental protection.

The present invention will now be further illuminated by combining with the appended drawings.

FIG. 1 is a structural schematic of the continuous ethanol separation device of the present invention. As is shown in the FIGURE, the device mainly comprises a housing 212, a screw conveyor for feeding 210 connecting with the inlet of the housing 212, a discharging bin 217 and a screw conveyor for discharging 218 connecting with the outlet of the housing 212, a rotation shaft 207 locating on the center axis of the housing 212 and a driving motor 201 connecting with the rotation shaft 207. Under the screw conveyor for feeding 210, on the inside wall of the housing 212 is provided with a distributing plate grid 208, which is a distributor consisting of several pieces of grid plates, and the fermentation materials inputted by the screw conveyor for feeding 210, after being distributed by the distributor, will be uniformly distributed in the rotary grid 213 on the surface of the tower tray 214. On the top of the rotation shaft is connected with plurality of tower trays 214 in series; the tower tray is a hollow body made up by two plates and a side wall, on the upper plate is uniformly distributed with gaps of $\phi 0.1$-5 mm for the steam passing through, on the tower tray is provided with several tower tray fan-shaped holes 215 for fermentation materials flowing, and tower tray rotary grid 213 made up by two cylinder plate grids connected by several of straight plate grids, the center of the rotary grid are fixed on the rotation shaft 207, which is throughout the center of each of the heating discs, and the rotary grid rotates along with the rotation shaft. The fan-shaped holes 215 on each of the tower trays 214 in the vertical direction successively shift a distance of the size of the fan-shaped hole opposite to the rotation direction of the rotary grid. Steam enters into each of the tower trays via the main line for steam inputting 216, is released from the gaps of the top plate of the tower tray, goes upwards along with the tower tray fan-shaped holes 215 of each of the tower trays 214, after fully contacting with the materials, runs to the steam outlet 211 on the upper of the housing, and enters into a rectifying tower via the steam outlet 211.

On the rotation shaft 207, under each of the tower trays 214 is connected with plurality of heating discs 214' in series coaxially with the tower trays 214, the heating disc 214' is a hollow body made up by two non-gapped plates and a side wall, and the chamber of the hollow body is provided with steam folding baffles 206, which uniformly distributes water vapor to improve the heat transfer efficiency with materials. The heating disk 214' on the sidewall is symmetrically provided with a steam inlet and a steam outlet, and on the heating disk 214' is provided with a heating disk rotary grid 213' and a heating disk fan-shaped hole 215' similarly to that on the tower trays 214. The heating disc 214' is air-tightly sealed, and the steam can only flow in or out from the inlet and outlet on the heating discs. The heating disk fan-shaped holes 215' on the heating disk 214' in the vertical direction successively shift a distance of the size of the fan-shaped hole opposite to the rotation direction of the heating disc rotary grid 213'. The steam inlet of the heating disc 214' is connected with the main line for steam inputting 216, and the steam outlet of the heating disc 214' is connected with the main line for steam outputting 205. The main line for steam outputting 205 at the end is provided with a gas-liquid separator 203, to separate steam and condensate.

The feeding inlet and discharging outlet of the housing 212 are both equipped with sealing apparatus, wherein the feeding inlet is sealed by fermentation material accumulation, and the discharging outlet is sealed with a flap valve 219, thus the entire device being air-tightly sealed. The temperature is kept via using thermal insulating materials on the outside wall of the housing 212, inputting steam into a jacket or using an electric heating zone, and the temperature is kept at 100° C. or above.

The continuous ethanol separation process from solid-state fermentation materials of the present invention is:

(a) The solid-state fermentation straw materials are fed into a distributing plate grid 208 at the top of the device via a screw conveyor for feeding 210, the materials uniformly distribute in the tower tray rotary grid 213 of the first layer of tower tray 214 at the top of the device and move along with it, to a tower tray fan-shaped hole 215 of the tower tray and then fall onto the rotary grid of the second layer of the tower tray, and so on until to the lowest layer of tower tray, during which the materials fully contact with steam to fulfill distillation. Through the lowest layer of tower tray, the materials fall onto the heating disc rotary grid 213' of the heating disc 214' and move along with it. When the materials move to the heating disk fan-shaped hole 215' of the heating disc 214', they fall onto the rotary grid of the next layer of heating disc, and so on until to the lowest layer of heating disc. On each of the heating discs 214', the materials do not contact with vapor, and are only heated by the heating discs to remove moisture, and through the plurality of heating discs 214', they are transferred to the discharging bin 217 at the bottom of the device. Then, the materials are outputted by the screw conveyor for discharging 218 and the double-layer flap valve 219, and the discharged materials are dried and recycled into a furnace to burn.

(b) In the meantime, saturated steam enters into the device via the main line for steam inputting 216 and spreads between each layer of tower trays and into the heating discs, the condensed water and the uncondensed steam after condensing and heat-releasing in the heating discs, after being collected by the main line for steam outputting 205, enter into the gas-liquid separator 203, the uncondensed steam is reused for its exhaust heat, and the condensed water after collected enters into a boiler through the water pipeline to oiler. Along with the steam transferring heat to the materials, ethanol and water are heated and vaporized into vapor, and the vapor directly enters into the rectifying tower via the output of the steam outlet 211 for rectifying.

In the device and process of the present invention, the distilled materials after drying recycle into a furnace to burn, so as to provide the source of heat for distillation. The rest of the materials can also be used as animal feed. This not only greatly saves energy and cost, but also avoids the effect of waste discharging to environment, being significant in environmental protection.

The results obtained in the practical production show that 16 tons of sweet sorghum straws are needed as the raw materials for producing 1 ton of ethanol, and 13.8 tons of residues will be produced after the raw material fermentation and distillation; using the method of the present invention, only 6.9 tons of the residues are needed when the fermented and distilled residues are used as fuel for providing energy, and the remain 6.9 tons of residues can also be used as animal feed. While in the prior art, due to coal being used as fuel, 0.5 ton of coal is usually needed for producing 1 ton of ethanol. In view of the above, the device and process of the present invention can greatly save energy costs, and have significant economic benefits.

EXAMPLES

Example 1

The device used in the present example comprises 14 layers of tower trays and 2 layers of heating discs; the steam line in the device is input with 0.4 MPa water vapor; after being stabilized, the device is input with solid-state fermentation materials of sweet sorghum straws at the speed of 5 t/h, wherein the ethanol content in the fermentation materials is 6% (by mass); the rotation speed of the rotation shaft is adjusted to make the fermentation materials having 35 min of residence time in the device; the stack height of the fermentation materials on the tower trays or heating discs is kept at 100-220 mm; and the reflux ratio is regulated at 0.1. After the system is stable, the distilled residues are sampled for ethanol content analysis, and the results show that the recovery rate of ethanol is 98.2%, the water content of the distilled materials is 70.4%.

Example 2

The device used in the present example comprises 9 layers of tower trays and 3 layers of heating discs; the steam line in the device is input with 0.4 MPa water vapor; after being stabilized, the device is input with solid-state fermentation materials of sweet sorghum straws at the speed of 3.5 t/h, wherein the ethanol content in the fermentation materials is 5% (by mass); the rotation speed of the rotation shaft is adjusted to make the fermentation materials having 25 min of residence time in the device; the stack height of the fermentation materials on the tower trays or heating discs is kept at 100-150 mm; and the reflux ratio is regulated at 0.15. After the system is stable, the distilled residues are sampled for ethanol content analysis, and the results show that the recovery rate of ethanol is 98.8%, the water content of the distilled materials is 62.1%.

Example 3

The device used in the present example comprises 6 layers of tower trays and 4 layers of heating discs; the steam line in the device is input with 0.4 MPa water vapor; after being stabilized, the device is input with solid-state fermentation materials of sweet sorghum straws at the speed of 2 t/h, wherein the ethanol content in the fermentation materials is 7% (by mass); the rotation speed of the rotation shaft is adjusted to make the fermentation materials having 20 min of residence time in the device; the stack height of the fermentation materials on the tower trays or heating discs is kept at 50-100 mm; and the reflux ratio is regulated at 0. After the system is stable, the distilled residues are sampled for ethanol content analysis, and the results show that the recovery rate of ethanol is 99.1%, the water content of the distilled materials is 57.6%.

What is claimed is:

1. A device for continuously separating fuel ethanol from solid-state fermentation materials, the device comprising:
    a housing (212),
    a screw conveyor for feeding (210) connecting with an inlet of the housing (212),
    a discharging bin (217) and a screw conveyor for discharging (218) connecting with an outlet of the housing (212),
    a rotation shaft (207) located on a center axis of the housing (212), and
    a driving motor (201) connecting with the rotation shaft (207),
    characterized in that:
        under the screw conveyor for feeding (210), on an inside wall of the housing (212) is provided a distributing plate grid (208);
        an inside of the housing (212) along the longitudinal direction has alcohol distillation components and drying components, wherein the drying components are located under the alcohol distillation components and connect with the alcohol distillation components, the alcohol distillation components are composed of a plurality of tower trays (214) connected in series with the rotation shaft, each of the plurality of tower trays (214) is a hollow body made up by two plates and a side wall, on an upper plate are uniformly distributed gaps of ϕ0.1-5 mm (or wire mesh sintering plate with a certain porosity) for steam passing through, and on each of the plurality of tower trays (214) are provided a tower tray rotary grid (213) and a tower tray fan-shaped hole (215);
        a steam inlet of the alcohol distillation components is located at the bottom of the alcohol distillation components, and a steam outlet is located at the top of the alcohol distillation components;
        the drying components are composed of a plurality of heating discs (214') connected in series with the rotation shaft, wherein each of the plurality of heating discs (214') is a hollow body made up by two plates and a side wall, and the chamber of the hollow body is provided with steam folding baffles (206), and is input with water vapor;
        the side wall of the heating disc (214') is symmetrically provided with a steam inlet and a steam outlet;
        each of the plurality of heating discs (214') is also provided with a heating disc rotary grid (213') and a heating disc fan-shaped hole (215');
        the steam inlets of the alcohol distillation components and the heating discs (214') are respectively connected with a main line for steam inputting (216), and the steam outlet of the alcohol distillation components is connected with an upper steam outlet (211) at the top of the housing, so that the steam directly enters into a rectifying tower for rectifying;
        the steam outlet of the drying components are connected with a main line for steam outputting (205) under the housing, and a main line for steam outputting (205) at the end is provided with a gas-liquid separator (203), to separate steam and condensate.

2. The device for continuously separating fuel ethanol from solid-state fermentation materials as claimed in claim 1, characterized in that: the plurality of heating disc fan-shaped holes (215') on the plurality of heating discs (214') in the vertical direction successively shift a distance of the size of the fan-shaped hole (215') opposite to rotation direction of the heating disc rotary grid (213').

3. The device for continuously separating fuel ethanol from solid-state fermentation materials as claimed in claim 1, characterized in that: the temperature inside the device is kept via using thermal insulating materials on the outside wall of the housing (212), using a jacket structure or an electric heating zone, and the temperature inside the device is kept at 100° C. or above.

4. The device for continuously separating fuel ethanol from solid-state fermentation materials as claimed in claim 1, characterized in that: the distributing plate grid (208) is a distributor consisting of several pieces of grid plates, and fermentation materials inputted by the screw conveyor for feeding (210), after being distributed by the distributor, will be uniformly distributed in the rotary grid on the surface of the heating disc.

5. The device for continuously separating fuel ethanol from solid-state fermentation materials as claimed in claim 1, characterized in that: the rotary grid (213, 213') is made up by two cylinder plate grids connected via several of straight plate grids, the center of the rotary grid (213, 213') is fixed on the rotation shaft (207) which goes throughout the center of each of the plurality of heating discs (214'), and the rotary grid (213, 213') rotates along with the rotation shaft (207).

6. The device for continuously separating fuel ethanol from solid-state fermentation materials as claimed in claim 1, characterized in that: each of the plurality of tower trays (214) is made up by perforated plate or wire mesh sintered plate.

* * * * *